United States Patent [19]

Hafner et al.

[11] Patent Number: 5,565,359

[45] Date of Patent: *Oct. 15, 1996

[54] CULTURES FOR PRODUCTION OF B AVERMECTINS

[75] Inventors: Edmund W. Hafner; Kelvin S. Holdom; S. Edward Lee, all of Groton, Conn.

[73] Assignee: Pfizer Inc., New York, N.Y.

[ * ] Notice: The term of this patent shall not extend beyond the expiration date of Pat. No. 5,234,831.

[21] Appl. No.: 448,159

[22] Filed: May 23, 1995

Related U.S. Application Data

[63] Continuation of Ser. No. 57,582, Apr. 30, 1993, abandoned, which is a continuation of Ser. No. 660,971, Feb. 26, 1991, Pat. No. 5,234,831, which is a continuation of Ser. No. 126,650, Dec. 1, 1987, abandoned, which is a continuation-in-part of Ser. No. 6,512, Jan. 23, 1987, abandoned.

[51] Int. Cl.[6] ................................................ C12N 1/20
[52] U.S. Cl. .................. 435/253.5; 435/119; 435/172.1; 435/172.2
[58] Field of Search ................................. 435/253.5, 119, 435/172.1, 172.2

[56] References Cited

U.S. PATENT DOCUMENTS

| | | | |
|---|---|---|---|
| 4,134,973 | 1/1979 | Fisher et al. | 424/180 |
| 4,156,720 | 5/1979 | Fisher et al. | 424/180 |
| 4,199,569 | 4/1980 | Chabala et al. | 424/180 |
| 4,285,963 | 8/1981 | Arison et al. | 424/279 |
| 4,310,519 | 1/1982 | Albers-Schonberg et al. | 424/181 |
| 4,328,335 | 5/1982 | Mrozik | 536/7.1 |
| 4,333,925 | 6/1982 | Buhs et al. | 536/7.1 |
| 4,378,353 | 3/1983 | Goegelman et al. | 424/181 |
| 4,423,209 | 12/1983 | Mrozik | 536/7.1 |
| 4,429,042 | 1/1984 | Albers-Schonberg et al. | 435/119 |
| 4,831,016 | 5/1989 | Mrozik | 514/30 |

FOREIGN PATENT DOCUMENTS

| | | |
|---|---|---|
| 1689 | 5/1979 | European Pat. Off. . |
| 2615 | 6/1979 | European Pat. Off. . |
| 7812 | 2/1980 | European Pat. Off. . |
| 214731 | 3/1987 | European Pat. Off. . |
| 215654 | 3/1987 | European Pat. Off. . |
| 235085 | 9/1987 | European Pat. Off. . |
| 241147 | 10/1987 | European Pat. Off. . |
| 58-78594 | 5/1983 | Japan . |
| 2166436 | 5/1986 | United Kingdom . |
| 2167751 | 6/1986 | United Kingdom . |
| 2170499 | 8/1986 | United Kingdom . |
| 2176182 | 12/1986 | United Kingdom . |

OTHER PUBLICATIONS

Burg, R. W. et al., Antimicrob. Agents Chemother. 15:361–367 (1979).
Chen, et al., Abstr. Pap. Am. Chem. Soc., 1983, 186 Meet. MBTD28.
Cheremisoff, P. N. and Ouellette, R. P., Eds. *Biotechnology*, 1985, Technomic Publishing Co., Inc., pp. 14–15.
Fisher & Mrozik, *Macrolide Antibiotics*, Academic Press (1984), Chp. 14.
Gray, P. P. et al., J. Ferm. Technol. 50:381–387 (1971).
Martin, et al., J. Bacteriology 115: 198–204 (1973).
*Manual of Methods for General Microbiology*, P. Gerhardt, Editor–in–Chief, American Society for Microbiology, Washington, D.C., 1981, pp. 365–370.
Ruby, et al., Sixth Int. Symp. on Actinomycete Biology, 1985, pp. 279–280.
Ruby et al., 6th Intnl. Symp. on "Biology of Actinomycetes", Debrecen, Hungary, Aug. 26–30 (1985).
Schulman et al., Antimicrobial Agents and Chemotherapy 29: 620–624 (1986).
Schulman et al., Antimicrobial Agents and Chemotherapy 31: 744–747 (1987).
Schulman, et al., Fed. Prac. 44: 931 (1985).
Schulman, et al., J. Antibiot. 38 (11): 1494–1498 (1985).
Tabor, et al., J. bact. 128: 485–486 (1976).
Willecke, et al., J. Biol. Chem. 246: 5264–5272 (1971).
Daum, S. J. et al., Ann. Rev. Microbiol. 33:241–265 (1979).
Schulman, M. D. et al., J. Antibiotics 34:541–549 (1986).

*Primary Examiner*—Irene Marx
*Attorney, Agent, or Firm*—Peter C. Richardson; Gregg C. Benson

[57] ABSTRACT

*Streptomyces avermitilis* lacking branched-chain 2-oxo acid dehydrogenase activity and avermectin B O-methyltransferase activity, method for preparation thereof, and use thereof to produce natural and non-natural B avermectins useful as parasiticides.

2 Claims, No Drawings

CULTURES FOR PRODUCTION OF B AVERMECTINS

CROSS REFERENCE TO RELATED APPLICATION

This application is a continuation of U.S. application Ser. No. 07/660,971, filed Feb. 26, 1991, now U.S. Pat. No. 5,234,831 which is a continuation of U.S. application Ser. No. 07/126,650, filed Dec. 1, 1987, now abandoned, which is a continuation-in-part of U.S. application Ser. No. 006,512, filed Jan. 23, 1987 now abandoned.

BACKGROUND OF THE INVENTION

1. Field of the Invention

This invention relates to *Streptomyces avermitilis* lacking avermectin B O-methyltransferase activity and branched-chain 2-oxo acid dehydrogenase activity, to methods for producing said *S. avermitilis* and to the use of *S. avermitilis* to produce natural and non-natural B avermectins.

2. Description of the Prior Art

U.S. Pat. Nos. 4,310,519 and 4,429,042 describe the avermectins, a complex of related agents having potent antiparasitic activity, and their production by aerobic fermentation of strains of *Streptomyces avermitilis*; namely, *S. avermitilis* ATCC Nos. 31267, 31271 and 31272. The last two strains cited represent a frozen vial and a lyophilized tube, respectively of a culture obtained by ultraviolet irradiation of *S. avermitilis* ATCC 31267.

EP 214,731, published Mar. 18, 1987, the counterpart of U.S. patent application Ser. No. 886,867, filed Jul. 16, 1986, discloses a number of compounds (referred to herein as non-natural avermectins) related to the natural or known avermectins but having a novel substituent group at the 25-position, and a process for their preparation by fermentation of an avermectin producing organism in the presence of certain specified carboxylic acids, or derivatives or precursors thereof. The *S. avermitilis* organisms used to produce the said novel C-25 substituted avermectins are *S. avermitilis* ATCC 31267, 31271, 31272 and NCIB 12121. The latter organism, described in EP 214,731, is derived from *S. avermitilis* ATCC 31271. It gives improved yields of the novel C-25 substituted avermectins when it is cultured in a semi-defined medium. Each of ATCC 31267, 31271, 31272 and NCIB 12121 may also produce, in addition to the novel C-25 substituted derivative, varying amounts of the known, or natural, avermectins wherein the 25-substituent is isopropyl or (S)-sec-butyl (1-methylpropyl).

The carbon skeleton of the avermectins (depicted in formula (I) below) is derived from acetates and propionates and the C-25 substituent of natural avermectins from L-isoleucine (R=(S)-sec-butyl) or L-valine (R=isopropyl) [Fisher and Mrozik, "Macrolide Antibiotics", Academic Press (1984) Ch 14].

By "known" or "natural" avermectins is meant those avermectins produced by *S. avermitilis* ATCC 31267, ATCC 31271 and ATCC 31272 wherein the 25-position substituent is either isopropyl or (S)-sec-butyl(1-methylpropyl). Avermectins wherein the 25-position substituent is other than isopropyl or sec-butyl (S-form) are referred to herein as novel or non-natural avermectins.

The strains of *S. avermitilis* cited in the above-mentioned U.S. patents produce a class of substances described generically therein as C-076. The class comprises eight distinct but closely related compounds described as C-076 A1a, A1b, A2a, A2b, B1a, B1b, B2a and B2b. The "a" series of compounds refers to the natural avermectins wherein the 25-substituent is (S)- sec-butyl and the "b" series to those wherein the 25-substituent is isopropyl. The designations "A" and "B" refer to avermectins wherein the 5-substituent is methoxy or hydroxy, respectively. Lastly, the numeral "1" refers to avermectins wherein a double bond is present at the 22-23 position; and numeral "2" to avermectins having a hydrogen at the 22-position and hydroxy at the 23 position.

In this application no such identifiers are used as regards the 25-substituent of the non-natural avermectins. Identifiers A1, A2, B1 and B2 have been retained to refer to non-natural avermectins having the structural features corresponding to those of the natural avermectins as noted above.

Generation of mutants devoid of branched-chain 2-oxo acid dehydrogenase activity has been reported for *Bacillus subtilis*, Willecke and Pardee, J. Biol. Chem. 246, 5264–72 (1971) and *Pseudomonas putida*, Martin et al., J. Bacteriology, 115 198–204 (1973), but not for Streptomyces.

*S. avermitilis* Agly-1, a mutant strain which produces virtually only avermectin aglycones A1a and A2a is reported by Schulman et al. J. Antibiot. 38(11), 1494–1498 (1985). Also reported is the fermentation of *S. avermitilis* Agly-1 in the presence of sinefungin which caused increased production of avermectin aglycone B components. Likewise, *S. avermitilis* 08, a high producing strain for avermectins, when fermented in the presence of sinefungin as inhibitor of O-methyl transferases, resulted in production of avermectins lacking O-methyl groups on the aglycone at C-5 and in the oleandrose disaccharide moiety.

U.S. Pat. No. 4,378,353 describes C-076 related compounds and their preparation by cultivation of MA-5218, a mutant strain of *S. avermitilis* ATCC 31272, obtained therefrom by ultraviolet irradiation. The mutant is identified as ATCC 31780. The C-076 related compounds produced by said mutant lack the C-076 furan ring. Additionally, in certain of the compounds reported, one or both of the oleandrose sugar moieties have been cleaved while in others the 5-position group was oxidized to a keto group.

Three classes of O-methyltransferase mutants of *S. avermitilis* that produce avermectins lacking O-methyl groups have been reported by Ruby et al., 6th International Symposium on the "Biology of Actinomycetes", Debrecen, Hungary, Aug. 26–30 (1985) and by Schulman et al, Antimicrobial Agents and Chemotherapy 31, 744–7 (1987). The first class produces primarily B avermectins due to their inability to methylate the C-5 hydroxyl of the macrocyclic lactone ring. The second class produces 3'-O, 3"-O-bis-demethylavermectins (avermectins lacking the O-methyl substituent at the 3 position of both oleandrose monosaccharide residues), and which are referred to as demethylavermectins. The third class is unable to methylate at any position.

Schulman et al., Fed. Proc. 44, 931 (1985) disclose increased production of B avermectins by fermenting *S. avermitilis* in the presence of substances such as sinefungin, S-adenosylethionine and S-adenosylhomocysteine which inhibit the methylation of the C-5 hydroxy group of the aglycone moiety by the enzyme avermectin B-O-methyltransferase. *Streptomyces avermitilis* mutants which lack O-methyltransferase activity and produce increased amounts of avermectin B components are also disclosed and referred to by Schulman et al. in Antimicrobial Agents and Chemotherapy 29, 620–624 (1986).

Mutagenesis of *S. avermitilis* produces mutants which lack branched-chain 2-oxo acid dehydrogenase activity. The mutants no longer possess the ability to produce significant amounts of the natural avermectins in the absence of added compound RCOOH wherein R is isopropyl or (S)-sec-butyl, or of a compound convertible to RCOOH during the fermentation process. Surprisingly and unexpectedly, however, the mutants have been found to produce avermectins, natural and non-natural, when fermented in the presence of an added compound R-COOH wherein R is isopropyl or (S)-sec-butyl, or other group disclosed herein, or of a precursor to said RCOOH. It is even more surprising that the herein described mutants which lack only branched-chain 2-oxo acid dehydrogenase activity, and which are unable to degrade L-isoleucine, L-leucine or L-valine, are able to assimilate a wide variety of compounds into the avermectin biosynthetic pathway with production of non-natural avermectins free of the presence of natural avermectins.

Mutagenesis of the thus-produced singly blocked mutants produces mutants which lack both branched-chain 2-oxo acid dehydrogenase activity and avermectin B-O-methyltransferase activity. Said doubly blocked mutants surprisingly and unexpectedly produce substantially only natural and non-natural B avermectins when cultivated in the presence of an added compound R-COOH where R is as defined above.

The natural avermectins, as noted, are produced as a complex mixture of eight distinct but closely related compounds; formula (I), R=isopropyl and (S)-sec-butyl. While they have been recovered in substantially pure form (see U.S. Pat. No. 4,429,042), the methodology is, at best, laborious. The B avermectins generally exhibit greater anthelmintic activity than do the corresponding A avermectins. The production of non-natural avermectins (A and B components) according to the process described in EP 214,731 may also produce some of the natural avermectins in varying amounts due to the presence of the branched-chain 2-oxo acid dehydrogenase and the amino acids L-valine and L-isoleucine in the cell of the S. avermitilis microorganisms and in the medium used in their production.

The ability to produce only the more bioeffective B components of either natural or non-natural avermectins, to minimize the number and complexity of the products, and by so doing to increase the purity of a chosen avermectin, and thereby to simplify separation procedures, is a desirable goal.

SUMMARY OF THE INVENTION

S. avermitilis strains lacking branched-chain 2-oxo acid dehydrogenase activity are produced by mutation of avermectin producing strains of S. avermitilis and especially by mutation of S. avermitilis ATCC 31267, ATCC 31271, ATCC 31272 or NCIB 12121. The mutants are unable to synthesize the natural avermectins except where the fatty acid, or a precursor thereto, bearing the isopropyl or sec-butyl (S-form) group is added to the medium in which the mutants are fermented. They are capable of producing natural and non-natural avermectins when fermented under aqueous aerobic conditions in a nutrient medium containing an appropriate primer acid or compound convertible thereto in the fermentation process.

Those mutants characterized by their lack of branched-chain 2-oxo acid dehydrogenase activity, are isolated from the mutagenized colonies on the basis of $^{14}CO_2$ In this procedure the absence of $^{14}CO_2$ evolution by permeabilized cells from a substrate of $[^{14}C\text{-}1]$-2-oxoisocaproic acid or $[^{14}C\text{-}1]$-2-oxo-3-methylvaletic acid or $[^{14}C\text{-}1]$-2-oxo-3-methylbutyric acid indicates absence of branched-chain 2-oxo acid dehydrogenase activity.

It was surprising and unexpected that the herein-described mutants lacking branched-chain 2-oxo acid dehydrogenase activity retained the ability to produce avermectins, especially non-natural avermectins. The inability of the mutants to produce the natural fatty acyl coenzyme A derivatives when grown on a conventional medium could have been a lethal mutation if membrane integrity depended upon said derivatives or if 2-oxo acid accumulation by the former mutant led to cytotoxicity. Furthermore, the mutants were not expected to be able to synthesize acetyl CoA and propionyl CoA from L-isoleucine and L-valine degradative metabolism as this requires the enzyme activities that the mutants are missing. The requirement for these acyl CoA derivatives for avermectin biosynthesis, noted above, led to the expectation that the mutants might be severely impaired in non-natural avermectin production, which, surprisingly, was not the case.

The lack of branched-chain 2-oxo acid dehydrogenase activity in the mutants described herein results in the prevention of branched-chain fatty acyl CoA synthesis from the degradation of L-isoleucine, L-leucine and L-valine and, thereby, the synthesis of the natural avermectins, except when acid R-COOH (wherein R is (S) sec-butyl or isopropyl), or a precursor therefore, is added to the fermentation medium.

Further mutation of the branched-chain 2-oxo acid dehydrogenase activity deficient mutants produces mutants which are, additionally, deficient in avermectin B O-methyltransferase activity. Mutants lacking avermectin B O-methyltransferase activity are unable to methylate the C-5 oxygen of the aglycone moiety of avermectins. Mutants lacking such activity produce essentially only B avermectins by preventing preparation of A avermectins.

The present invention also includes any organism, regardless of its appearance or physiological behavior, that may be developed by means of transformation, transduction, genetic recombination or some other genetical procedure, using a nucleic acid or an equivalent material from the herein described species, whereby it has acquired the characteristics of the herein described mutants.

The terms "avermectin" or "avermectins" as used herein refers to compounds having formula (I) below but wherein the 25-substituent (R) can be any group assimilable at said position by the S. avermitilis of this invention.

The herein described mutants are highly valuable for producing non-natural B avermectins by the processes disclosed and exemplified herein. They are especially valuable for production of preferred avermectins, i.e., compounds wherein the C-25 substituent is $C_4$–$C_6$ cycloalkyl or cycloalkenyl, optionally substituted by $C_1$–$C_4$ alkyl group; 1-methylthioethyl, or a 5- or 6-membered oxygen or sulfur heterocyclic group, especially 3-thienyl or 3-furyl.

DETAILED DESCRIPTION OF THE INVENTION

Mutation of an avermectin producing member of the species Streptomyces avermitilis is carried out according to known procedures using any of a variety of mutating agents including ultraviolet irradiation, X-ray irradiation, N-methyl-N'-nitro-N-nitrosoguanidine, ethylmethane sulfonate, nitrous acid and nitrogen mustards, e.g., N-methylbis(2-chloroethyl)amine, or like treatments. The mutagenesis can be conducted on spores or on a vegetative culture of S. avermitilis capable of producing natural avermectins, e.g., S. avermitilis ATCC 31272.

Following procedures well known to those skilled in the art, mutagenized colonies are selected for lack of branched-chain 2-oxo acid dehydrogenase on the basis of a biochemical assay method which permits screening of large numbers of randomly mutagenized bacterial colonies for $^{14}CO_2$ production from selected [$^{14}C$-1]-2-oxo branched-chain acids (Tabor et al., J. Bact. 128, 485–486, 1976).

The methodology comprises growing the mutant colonies in the wells of a microtiter plate on a suitable nutrient medium, permeabilizing the cells with toluene followed by adding the [$^{14}C$-1]-2-oxo acid (e.g. 2-oxoisocaproic acid) to each well and checking the atmosphere above the fermentation for $^{14}CO_2$. Alternatively, [$^{14}C$-1]-2-oxo-3-methylvaleric acid, or [$^{14}C$-1]-2-oxo-3-methylbutyric acid can be used in place of [$^{14}C$-1]-2-oxo-isocaproic acid. Production of $^{14}CO_2$ is conveniently checked for by placing moist $Ba(OH)_2$-saturated filter paper above the individual wells to trap any $^{14}CO_2$ released and detection of $Ba^{14}CO_3$, if any, by autoradiography. Mutants which lack branched-chain 2-oxo acid dehydrogenase activity give autoradiograms approximating those of blank (uninoculated) controls; i.e., no additional $Ba^{14}CO_3$ is produced by the mutants.

The mutants thus obtained are subjected to further mutagenesis using any of the above-mentioned mutating agents. Mutagenized colonies are assayed for lack of avermectin B O-methyltransferase activity by chromatography (thin layer or high performance liquid chromatography) after fermentation in the presence of added precursor (e.g. 2-methylbutyric acid). Avermectin A compounds are essentially absent from fermentation broths of such mutants.

In addition to production of desired alleles of a given strain of microorganism by mutagenesis, protoplast fusion permits introduction of desirable alleles produced/identified in one strain into the chromosome of another strain. For example, a strain of S. avermitilis deficient in branched-chain 2-oxo acid dehydrogenase and avermectin B O-methyltransferase can, by protoplast fusion with a S. avermitilis strain having the aforementioned activities, produce a strain of S. avermitilis deficient only in avermectin B O-methyltransferase activity. As those skilled in the art recognize, protoplast fusion technology enables combination of desirable alleles from divergent lines of selection into a single strain.

The morphological and cultural characteristics of the mutants of this invention are generally as described in U.S. Pat. No. 4,429,042. The distinguishing characteristic of the mutants of this invention is their lack of branched-chain 2-oxo acid dehydrogenase activity and of avermectin B O-methyltransferase activity which characteristics are determined as described herein. The lack of said activities results in the failure of the mutants to produce the natural B avermectins when grown on a defined medium substantially free of fatty acids RCOOH wherein R is isopropyl or (S)-sec-butyl, or compounds convertible to said RCOOH during fermentation. A taxonomic investigation conducted by the American Type Culture Collection, confirmed that the characteristics of mutant strain I-3, selected by the above $^{14}CO_2$ assay, bears a close relationship to those of the parental ATCC 31272 strain described in U.S. Pat. No. 4,429,042, but with certain exceptions. Thus, mutant strain I-3 (ATCC 53567) forms significantly fewer spore chains than does ATCC 31272. In experiments by applicants, raffinose did not appear to support the growth of I-3. In contrast to the description given for ATCC 31272 in U.S. Pat. No. 4,429,042, we are unable to detect growth of the mutant or of ATCC 31272 with sucrose as sole carbon source. Mutant I-3 is deficient in branched-chain 2-oxo acid dehydrogenase activity. The doubly deficient mutant of this invention, S. avermitilis 7881, which lacks branched-chain 2-oxo acid dehydrogenase activity and avermectin B O-methyltransferase activity, produced by further mutagenesis of mutant I-3 (ATCC 53567), bears a similar taxonomic relation to ATCC 31272 as does mutant strain I-3.

Streptomyces avermitilis I-3 and 7881 have been deposited under the terms of the Budapest Treaty in the American Type Culture Collection, Rockville, Md., a recognized depository affording permanence of the deposits and ready accessibility thereto by the public if a patent is granted on this application. They have been given the designation Streptomyces avermitilis ATCC 53567 and ATCC 53692, respectively. The deposits are available during pendency of this application to one determined by the Commissioner of the United States Patent and Trademark Office to be entitled thereto under 37 CFR 1.14 and 35 USC 122, and in accordance with foreign patent laws in countries wherein counterparts of this application, or its progeny, are filed. All restrictions on the availability to the public of the microorganisms deposited will be irrevocably removed upon granting of the patent.

Each of S. avermitilis ATCC 31267, ATCC 31271, ATCC 31272 and NCIB 12121 produces the natural avermectins, formula (I) compounds

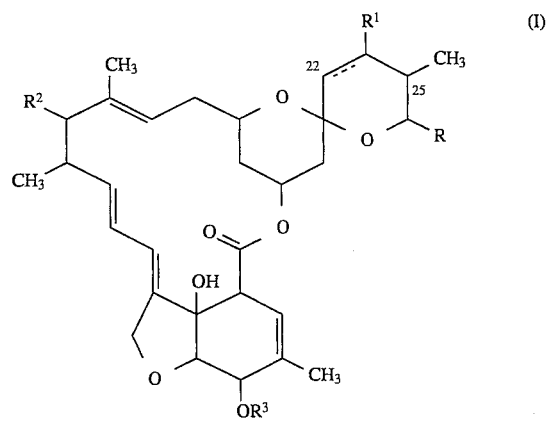

wherein the broken line at the 22-23 position represents an optional double bond;

R$^1$ is hydroxy and is present only when the double bond is absent;

R$^2$ is 4'-(alpha-L-oleandrosyl)-alpha-L-oleandrosyloxy of the formula

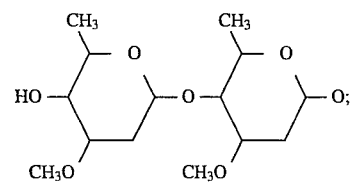

R$^3$ is hydrogen or methyl; and

R is isopropyl or (S)-sec-butyl. U.S. Pat. No. 4,285,963 describes an avermectin of formula (I) wherein the 25-position is substituted with a methyl and an ethyl group; R$^1$ is hydroxy and R$^3$ is methyl.

In the non-natural avermectins referred to herein R is a substituent other than isopropyl or (S)-sec-butyl and is as defined below.

The compounds essential for utilization in the biosynthesis of formula (I) compounds occur in the cell of S. avermitilis and in the medium. These compounds arise from degradation of L-valine and L-isoleucine or from their corresponding 2-oxo acids via decarboxylation of the 2-oxo acid by branched-chain 2-oxo acid dehydrogenase, concomitant with coupling the product with coenzyme A. Their presence accounts for the concurrent production of both the isopropyl and (S)-sec-butyl compounds of formula (I). This, of course, gives rise to problems in separating the isopropyl from the (S)-sec-butyl derivatives.

When fermented in a nutrient medium containing the appropriate primer compound the mutants of this invention produce a compound of formula (I) or, as is more usually the case, a mixture of two compounds of formula (I) in which R corresponds to the primer compound used. Up to two products, conveniently and trivially referred to as R-avermectin B1 and B2, according to the designations used in U.S. Pat. No. 4,429,042, can be produced. The "R-" group, of course, refers to the C-25 substituent. For example, when R is cyclopentyl the two possible avermectins are:

| Trivial Name | $R^1$ | $R^3$ |
|---|---|---|
| cyclopentyl avermectin B1 | double bond | H |
| cyclopentyl avermectin B2 | hydroxy | H |

In the non-natural avermectins the C-25 substituent "R" of formula (I) is other than isopropyl or (S)-sec-butyl.

Compounds of formula (I) wherein the double bond is present and OH is absent may alternatively be prepared from the corresponding compound of formula (I) wherein $R^1$ is OH and the double bond is absent by a dehydration reaction. The reaction is performed by first selectively protecting the hydroxy groups at the 5 and 4" positions, e.g. as the t-butyldimethylsilyloxy acetyl derivative, then reacting with a substituted thiocarbonyl halide, such as (4-methylphenoxy)thiocarbonyl chloride, followed by heating in a high boiling point solvent, e.g. trichlorobenzene, to effect the dehydration. The product is finally deprotected to give the unsaturated compound. These steps together with appropriate reagents and reaction conditions are described in U.S. Pat. No. 4,328,335.

Compounds of formula (I) wherein $R^1$ is H and the double bond is absent can be prepared from the corresponding compound wherein the double bond is present and $R^1$ is absent, by selective catalytic hydrogenation using an appropriate catalyst. For example, the reduction may be achieved using tris(triphenylphosphine)rhodium (I) chloride as described in European Patent Application Publication No. 0001689, and its counterpart U.S. Pat. No. 4,199,569, issued Apr. 22, 1980.

The compounds of formula (I) wherein $R^2$ is H are prepared from the corresponding compounds wherein $R^2$ is 4'-(alpha-L-oleandrosyl)-alpha-L-oleandrosyloxy by removing the 4'-(alpha-L-oleandrosyl)-alpha-L-oleandrose group by mild hydrolysis with an acid in an aqueous organic solvent to yield the aglycone having a hydroxy group at the 13-position; this is then halogenated, for example by reaction with a benzene sulfonyl halide, to yield the 13-deoxy-13-halo derivative which is finally selectively reduced, for example using tributyltin hydride. In order to avoid unwanted side reactions it is desirable to protect any other hydroxy groups which may be present, for example using a tert-butyldimethylsilyl group. This is then readily removed after the halogenation or reduction step by treatment with methanol containing a trace of acid. All these steps together with appropriate reagents and reaction conditions for their performance are described in European Patent Application Publication No. 0002615.

The compounds capable of utilization by the *S. avermitilis* of this invention for the biosynthesis of avermectins, natural and non-natural, are compounds of formula (II-A)

R—COOH    (II-A), including compounds convertible to (II-A) during the fermentation process. Said compounds are referred to herein as "primer compounds". In formula (II-A), R is an alpha-branched-chain group, the carbon atom thereof to which is attached the —COOH group is also attached to at least two other atoms or groups other than hydrogen. This definition, of course, embraces saturated and unsaturated acyclic and cyclic groups, including those optionally bearing a sulfur or oxygen heteroatom as a member of the acyclic chain or cyclic ring.

More specifically, R, which becomes the C-25 substituent, can be an alpha-branched $C_3$–$C_8$ alkyl, alkenyl, alkynyl, alkoxyalkyl or alkylthioalkyl group; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms (fluoro, chloro, iodo or bromo); or a 3 to 6 membered oxygen or sulfur containing heterocyclic ring which may be saturated, or fully or partially unsaturated and which may optionally be substituted by one or more $C_1$–$C_4$ alkyl groups or halo atoms.

Compounds convertible to RCOOH; i.e., precursors, in the fermentation process are compounds of formulae (II-B) wherein R is as defined above:

R—(CH$_2$)$_n$—Z    (II-B)

n is 0, 2, 4 or 6; and Z is —CH$_2$OH, —CHO, —CH$_2$NH$_2$, —COOR$^4$ or —CONHR$^5$ wherein R$^4$ is H or (C$_{1-6}$)alkyl; R$^5$ is hydrogen (C$_{1-4}$)alkyl, or the residue of an amino acid, especially of aspartic acid, glutamic acid and methionine, e.g., —CH(COOH)CH$_2$COOH, —CH(COOH)(CH$_2$)$_2$COOH and —CH(COOH)(CH$_2$)$_2$SCH$_3$, respectively.

Also included in this invention are the isomeric forms of formula (II-A) compounds, and compounds convertible thereto during the fermentation process, and the isomeric avermectins at C-25 resulting from their use in the herein described process.

The process of this invention is carried out by aerobic fermentation with a strain of *S. avermitilis* which lacks branched-chain 2-oxo acid dehydrogenase activity and avermectin B-O-methyltransferase activity in an aqueous nutrient medium comprising an assimilable source of nitrogen, carbon, inorganic salts and a compound of formula RCOOH, or a compound convertible to said compound (i.e., a precursor) during the fermentation. The acid, or compound convertible thereto, is added to the fermentation either at the time of inoculation or at intervals during the fermentation. Production of the avermectin products may be monitored by removing samples from the fermentation, extracting with an organic solvent and following the appearance of the product by chromatography, for example using high pressure liquid chromatography. Incubation is continued until the yield of the product has been maximized, generally for a period of from 4 to 15 days.

A preferred level of each addition of the primer compounds (carboxylic acid or compound convertible thereto) is between 0.05 and 3.0 grams per liter. The primer compound can be added continuously, intermittently or all at once to the fermentation. The acid (RCOOH) is added as such or as a salt, such as the sodium, lithium or ammonium salt, or as a compound convertible to the acid as defined above. The acid, if a solid, is preferably dissolved in a suitable solvent such as water or ($C_{1-4}$)alcohols.

The media used for the fermentation can, especially when the C-25 substituent is to be isopropyl or (S)-sec-butyl, be conventional media containing assimilable sources of carbon, nitrogen and trace elements. When the C-25 substituent is to be a non-natural group; i.e., it is not isopropyl or (S)-sec-butyl, the fermentation medium is one in which the chosen ingredients lack, or contain only minimal amounts of primer compounds wherein the R moiety is isopropyl or (S)-sec-butyl.

After fermentation for a period of several days at a temperature preferably in the range of 24° to 33° C., the fermentation broth is centrifuged or filtered and the mycelial cake is extracted with preferably acetone or methanol. The solvent extract is concentrated and the desired product is then extracted into a water-immiscible organic solvent, such as methylene chloride, ethyl acetate, chloroform, butanol or methyl isobutyl ketone. The solvent extract is concentrated and the crude product is further purified as necessary by chromatography, for example using preparative reverse phase, high pressure liquid chromatography.

The product is generally obtained as a mixture of the compounds of formula (I) wherein $R^2$ is 4'- (alpha-L-oleandrosyl)-alpha-L-oleandrosyloxy, $R^1$ is OH and the double bond absent or $R^1$ is absent and the double bond is present and wherein $R^3$ is H. Compounds wherein $R^3$ is $CH_3$ are essentially absent. However, the proportions of each compound can vary depending on the particular mutant and primer compound employed and the conditions used.

The source of the R group; i.e., whether it comes directly from R—COOH or is produced from one of the above precursors, or from any precursor, is immaterial to the production of the avermectins. The critical requirement of the process of this invention for their production is that the desired R group be made available to the *S. avermitilis* strains of this invention in the fermentation process. Suitable compounds include the following:
2,3-dimethylbutyric acid
2-methylhexanoic acid
2-methylpent-4-enoic acid
2-cyclopropyl propionic acid
4,4-difluorocyclohexane carboxylic acid Lithium salt
4-methylenecyclohexane carboxylic acid
3-methylcyclohexane carboxylic acid (cis/trans)
1-cyclopentene carboxylic acid
1-cyclohexene carboxylic acid
tetrahydropyran-4-carboxylic acid
thiophene-2-carboxylic acid
3-furoic acid
2-chlorothiophene-4-carboxylic acid
cyclobutane carboxylic acid
cyclopentane carboxylic acid
cyclohexane carboxylic acid
cycloheptane carboxylic acid
2-methylcyclopropane carboxylic acid
3-cyclohexene-1-carboxylic acid
2-methylthiopropionic acid
2-methyl-4-methoxybutyric acid
thiophene-3-carboxylic acid
hydroxymethylcyclopentane
3-thiophene carboxaldehyde
3-cyclohexylpropionic acid
3-cyclopentylpropionic acid
hydroxymethylcyclobutane
tetrahydrothiophene-3-carboxylic acid
3-cyclopentyl-1-propanol
3-methylcyclobutane carboxylic acid Lithium salt
3-fluorocyclobutane carboxylic acid
3-methylenecyclobutane carboxylic acid Lithium salt
2-methyl-4-methylthiobutyric acid
tetrahydrothiopyran-4-carboxylic acid
cyclobutylmethylamine
ethyl cyclobutanecarboxylate
4-hydroxymethylcyclopentene
2-(3-thiophenecarbonyl)propionic acid ethyl ester
S-2-methylpentanoic acid
R-2-methylpentanoic acid Three classes of O-methyltransferase mutants can be obtained from the herein-described branched-chain 2-oxo acid dehydrogenase negative mutants. Mutants in which a mutation in active branched-chain 2-oxo acid dehydrogenase activity is combined with one or more of the O-methyltransferase mutations, to yield strains of *S. avermitilis* that will, when fed RCOOH compounds or compounds convertible to RCOOH during the fermentation process, produce primarily B avermectins, demethyl-avermectins or avermectins which have not been methylated at all. Said mutants are obtained by mutagenesis of the herein described mutants which lack branched-chain 2-oxo acid dehydrogenase activity by means of ultraviolet light and/or chemical mutagens such as N-methyl-N-nitrosourethan, nitrosoguanidine or other agent such as those enumerated above. Alternatively, branched-chain 2-oxo acid dehydrogenase positive mutants which lack one or more of the O-methyltransferases can be mutated by treatment with UV light or a mutagenizing agent to produce the branched-chain 2-oxo acid dehydrogenase negative mutants.

The non-natural avermectins produced by such mutants are characterized by the presence of hydroxy groups at the C-5 position of the aglycone moiety and/or the C-3' and/or C-3" positions of the oleandrose moieties.

The above-described mutants are identified according to the methodology described by Schulman et al. Antimicrobial Agents and Chemotherapy, 29, 620–624 (1986). They are useful for the same purposes and in the same way as are the known avermectins.

Alternatively, increased amounts of the B avermectins, including those lacking methyl groups on the oleandrose disaccharide moiety, are produced by fermenting the mutants of this invention, which lack active branched-chain 2-oxo acid dehydrogenase, in the presence of a substance such as sinefungin, S-adenosylethionine or S-adenosylhomocysteine which inhibit O-methyltransferase activity.

The compounds of the invention are highly active antiparasitic agents having particular utility as anthelmintics, ectoparasiticides, insecticides and acaricides.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastro-intestinal parasites such as Ancylostoma, Necator, Ascaris, Strongyloides, Trichinella, Capillaria, Trichuris, Enterobius and parasites which are found in the blood or other tissues and organs such as filarial worms and the extra intestinal stages of Strongyloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars and against migratory orthopterans such as locusts.

The compounds of formula (I) are administered as a formulation appropriate to the specific use envisaged and to the particular species of host animal being treated and the parasite or insect involved. For use as an anthelmintic the compounds may be administered orally in the form of a capsule, bolus, tablet or a liquid drench, or alternatively, they may be administered by injection or as an implant. Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc, magnesium stearate etc. A drench formulation may be prepared by dispersing the active ingredient in an aqueous solution together with dispersing or wetting agents, etc., and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally for oral administration a dose of from about 0.001 to 10 mg per kg of animal body weight given as a single dose or in divided doses for a period of from 1 to 5 days will be satisfactory, but, of course, there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, emulsions and the like in accordance with standard agricultural practice.

Production of *S. avermitilis* I-3 (ATCC 53567)

Step 1. *S. avermitilis* ATCC 31272 was grown as a confluent lawn on New Patch Agar Medium for 12 days at 30° C. The medium comprised

| V-8 Juice* | 200 ml |
| --- | --- |
| CaCO$_3$ | 3 grams |
| Agar | 15 grams |
| H$_2$O to | 1000 ml |
| Nutrient broth | 1.0 grams/L |
| sodium acetate.3H$_2$O | 1.4 grams/L |
| isovaleric acid | 50 mg/L |
| isobutyric acid | 50 mg/L |
| methylbutyric acid | 50 mg/L |
| isoleucine | 250 mg/L |
| leucine | 250 mg/L |
| valine | 250 mg/L |
| trace elements solution** | 1 ml/L |

*A mixture of 8 vegetable juices (tomato, carrots, celery, beets, parsley, lettuce, watercress and spinach) plus salt, ascorbic and citric acids and natural flavors. Available from Campbell Soup Company, Camden, NJ.
**Composition of Trace elements solution:

| FeCl$_3$.6H$_2$O | 2.7 g |
| --- | --- |
| MnSO$_4$.H$_2$O | 4.2 |
| CuSO$_4$.5H$_2$O | 0.5 |
| CaCl$_2$ | 11.0 |
| H$_3$BO$_3$ | 0.62 |
| CoCl$_2$.6H$_2$O | 0.24 |
| ZnCl$_2$ | 0.68 |
| Na$_2$MoO$_4$ | 0.24 |

Dissolve the above in 1 liter of 0.1N HCl.

Spores were harvested from 3 such plates and suspended in 20 ml. of 0.05M tris-maleic acid buffer, pH 9.0.

Step 2. 10 ml of the spore suspension was added to a vial containing 10 mg of N-methyl-N'-nitro-N-nitrosoguanidine (NTG). The vial was incubated and shaken at 28° C. for 60 minutes and the spores then washed profusely with 1% NaCl solution.

Step 3. The washed spores were suspended in 1% NaCl and mixed with an equal volume of 80% ethylene glycol. This suspension was preserved at −20° C. and used as a source of cells to be screened for mutants. It gave approximately $10^4$ colonies/ml when germinated.

This spore stock was spread on YPD plates to yield approximately 100 colonies per plate (YPD medium comprises 10 g/l of each of yeast extract, Bacto peptone* and dextrose; and 15 g/l of Bacto agar*, adjusted to pH 6.9 before autoclaving). Ingredients marked with an asterisk are available from Difco Laboratories, Detroit, Mich. 48238.

Step 4. Single colonies were picked from plates after 2–3 weeks of growth at 28° C. and placed in individual wells of a standard 96 well microtiter plate. Also, a small quantity of the colony was patched onto a fresh agar medium to serve as a source of viable cells when mutants are identified.

Step 5. To each well was added approximately 75 microliters of a liquid M9 salts medium containing 1% glucose, 0.1% casamino acids, and 0.01% of each of isovaleric, isobutyric and 2-methylbutyric acids. After several days of incubation at 28° C., the cells were assayed for the presence of branched-chain 2-oxo acid dehydrogenase. (Each liter of M9 salts medium comprises 6 g Na$_2$HPO$_4$, 3 g KH$_2$PO$_4$, 0.5 g NaCl and 1 g of NH$_4$Cl. The medium is autoclaved and then 1 ml of each of sterilized 1M MgSO$_4$ and 0.1M CaCl$_2$ are added aseptically).

Step 6. A microsuspension of 5% toluene in M9 salts medium was prepared by a brief sonication of the immiscible mixture. To 25 ml of this suspension was added 1.2 ml of a solution containing [$^{14}$C-1]-2-oxoisocaproic acid, 2.5 microcurie/ml and 10.0 microcurie/micromole. 50 Microliters of this overall mixture was added to each of the wells of the microtiter plates containing the colonies to be assayed.

Step 7. The $^{14}$CO$_2$ produced from each well was trapped and visualized by the procedure described by Tabor et al., *J. Bacteriol.* 128 485–486 (1976) entitled "Convenient Method for Detecting $^{14}$CO$_2$ in Multiple Samples: Application to Rapid Screening for Mutants". Mutants lacking active branched-chain 2-oxo acid dehydrogenase produce no Ba$^{14}$CO$_3$ beyond that observed for the controls.

A more refined method which improves the contrast between a positive assay for $^{14}$CO$_2$, indicated by a dark spot on the autoradiogram as a result of Ba$^{14}$CO$_3$ formation, and a negative assay indicated by no spot or a very light spot, comprises the following modified screen.

Single colonies (see Step 4 above) were picked from the agar medium after 7–14 days of growth (rather than 2–3 weeks and assayed directly by steps 6 and 7 above). Step 5 of the above procedure is omitted.

An even more refined assay method which is quantitative in nature as regards $^{14}CO_2$ release comprises growing the mutants detected by the above screens on a suitable medium comprising M9 salts medium with glucose, 1% and "Syncasa-bcaa", 0.1% (a synthetic mixture of L-amino acids with the approximate composition of commercial casamino acids, but without the presence of L-valine, L-isoleucine and L-leucine, see below).

After growth to high cell density, the cells were washed in M9 salts medium and resuspended in cold M9 salts medium containing 1% toluene which had been sonicated to produce a milky white dispersion of the toluene. The cell/buffer/toluene suspension was incubated for 40 minutes at 30° C. in order to permeabilize the cells. The permeabilized cells were then washed in M9 medium salts and finally resuspended in one-fifth the original volume of M9 medium buffer. 180 Microliters of this suspension were used per assay.

A reaction volume of 300 microliters contained the toluenized cells, thiamine pyrophosphate (TPP), 0.4 mM; coenzyme A (CoA), 0.11 mM; nicotinamide adenine dinucleotide (NAD), 0.68 mM, dithiothreitol (DTT), 2.6 mM; $MgCl_2$, 4.1 mM; Tris-HCl, 60 mM; Tris-HCl, 60 mM, pH 7.5; and [$^{14}C$-1]-2-oxoisocaproate, 6,000 cpm, microcurie per micromole. The efficiency of counting was 73%. The reaction was carried out in 15 ml scintillation vials containing a 2×2 cm Whatman #4 paper square pressed into the screw cap of the vial. The paper contains 30 microliters of 1M Hyamine Hydroxide (1M solution of methylbenzethonime hydroxide in methanol; available from Sigma Chemical Co., St. Louis, Mo. 63178) which traps $^{14}CO_2$ evolved in the reaction. After incubation for 2 hours, the papers are immersed in 10 ml of Beckman Aquasol II (Universal LSC (liquid scintillation counter) available from New England Nuclear Research Products, Boston, Mass. 02118) and the radioactivity measured in a liquid scintillation counter after equilibration in this solvent for 4 hours or more. A blank control reaction (i.e.—no cells) gives ca. 50–300 cpm.

Mutant I-3 and others like it gave counts that were less than or equal to the blank control reaction, whereas the parent strain gave counts several fold higher than blank control value.

| Composition of "Syncasa - bccaa", 100 fold Concentrate | |
| --- | --- |
|  | grams/liter |
| L-alanine | 3 |
| L-arginine | 4 |
| L-aspartic acid | 6 |
| L-cystine | 1 |
| L-glutamic acid | 20 |
| glycine | 1 |
| L-histidine | 2 |
| L-lysine | 7 |
| L-methionine | 3 |
| L-phenylalanine | 6 |
| L-proline | 10 |
| L-serine | 6 |
| L-threonine | 4 |
| L-tyrosine | 4 |
| L-tryptophan | 1 |

The mixture is adjusted to pH 7 and filter sterilized. One volume of concentrate is added to 99 volumes of medium to achieve standard use concentrations.

Production of Doubly Blocked Mutants of *S. avermitilis* 7881 (ATCC 53692) Deficient in Branched-Chain 2-Oxo Acid Dehydrogenase and in Avermectin B O-Methyltransferase Step 1. *S. avermitilis* ATCC 53567 was grown as a confluent lawn on New Patch Agar Medium for 12 days at 30° C.

Spores were harvested from 3 such plates and suspended in 20 ml. of 0.05M tris-maleic acid buffer, pH 9.0.

Step 2. 10 ml of the spore suspension was added to a vial containing 10 mg of N-methyl-N'-nitro-N-nitrosoguanidine (NTG). The vial was incubated and shaken at 28° C. for 60 minutes and the spores then washed profusely with 1% NaCl solution.

Step 3. The washed spores were suspended in 1% NaCl and mixed with an equal volume of 80% ethylene glycol. This suspension was preserved at −20° C. and used as a source of cells to be screened for mutants.

This spore stock was spread on YPD plates to yield approximately 100 colonies per plate. Colonies of the mutagenized population (nitrosoguanidine treated) of *Streptomyces avermitilis* strain I-3 (ATCC 53567) are picked, and spread as patches on an agar medium prepared as follows (grams per liter): thinned starch, 80; $K_2HPO_4$, 1; $MgSO_4 \cdot 7H_2O$, 1; ardamine PH, 5; $CaCO_3$, 5; P-2000, 1 ml; $FeSO_4 \cdot 7H_2O$, 0.01; $MnCl_2 \cdot 4H_2O$, 0.001; $ZnSO_4 \cdot 7H_2O$, 0.001; Bacto agar, 17; distilled $H_2O$ to 980 ml. The pH is adjusted to 7.0 with NaOH prior to autoclaving at 121° C. for 20 minutes. After autoclaving, 20 ml of a sterile 5% stock solution of (±)-2-methylbutyric acid, pH 7.0 is added.

The agar cultures are incubated 8 to 12 days at 28° C. Cells (mycelia) are removed from the agar surface, and put into 250 microliters of acetone. Twenty-five (25) microliters of the acetone extracts are then spotted on Analtech Silica Gel GF precoated thin layer chromatography plates. The chromatogram is run for 30 to 40 minutes with ethyl acetate as solvent, then dried, and sprayed with 3% vanillin in ethanol. The plates are placed in a 100° C. oven for 1 to 3 minutes, then sprayed with 3% sulfuric acid in ethanol, and again placed in a 100° C. oven for 10 to 15 minutes. Mutants deficient in avermectin B O-methyltransferase are identified by a change in the chromatographic pattern; i.e., the spots corresponding to avermectin B components (Rf ca 0.54, 0.42 for B1 and B2, respectively) are still present, but the spots corresponding to avermectin A components (Rf ca 0.69, 0.58 for A1 and A2, respectively) are missing.

General High Performance Liquid Chromatography (HPLC) Procedures

Mobile Phase:

150 ml of water 70 ml of acetonitrile bring to 1 liter with methanol

Column:

Ultrasphere ODS 25 cm (Beckman Instruments, Fullerton, Calif. 92634-3100)

flow: 0.75 ml/minute detection: UV a 240 nm attenuation: near 6

Sample diluent (D):

35 ml acetonitrile plus 390 ml methanol

Standards:

1. weigh 0.5 mg avermectin A2A into 10 ml flask and bring to volume with methanol 2. weigh 0.5 mg test product into 10 ml flask and bring to volume with methanol 1 and 2 are standard stock solutions; for standard solution to run:

take 100 ul (1) and 100 ul (2) into a vial add 800 ul mobile phase

Samples:

1. Take 1 ml of well shaken broth; spin down
2. Remove as much supernatant as possible without disturbing pellet
3. Add 100 ul of HPLC water to the pellet and vortex mix to disperse
4. Add 2 ml diluent (D) and mix well
5. Filter the same and run on HPLC.

The natural and non-natural avermectins described herein were subjected to this HPLC chromatographic procedure and the retention time of the peaks of the individual avermectins divided by the retention time observed for the oligomycin A present and which serves as internal standard for a given HPLC determination. Oligomycin A is almost always observed by HPLC as by-product of *S. avermitilis* fermentations and is the only product seen on HPLC produced by the mutants described herein when they are cultured in a medium free of acids RCOOH wherein R is as defined herein or in medium free of compounds convertible to acids of the formula RCOOH wherein R is as defined herein. Typically, oligomycin A retention time is 12.5–14 minutes. The ratio of the retention times (RT) affords a more significant basis for comparing the identity and yields of avermectin products. The general order of appearance of the avermectin products on HPLC is B2, A2, B1 and A1.

| Natural Avermectin | RT/RT (oligomycin A) |
|---|---|
| B2b | 0.70 |
| B2a | 0.84 |
| A2b | 0.90 |
| A2a | 1.09 |
| B1b | 1.40 |
| B1a | 1.83 |
| A1b | 1.83 |
| A1a | 2.42 |

Note that B1a and A1b are unresolved.

| Non-Natural Avermectin | RT/RT (oligomycin A) |
|---|---|
| cyclopentyl B2 | 0.94 |
| cyclopentyl A2 | 1.23 |
| cyclopentyl B1 | 1.99 |
| cyclopentyl A1 | 2.62 |

Retention times vary 1–2 minutes on different days, with oligomycin A generally appearing near 12.5–14 minutes.

In the following examples the avermectins were determined by the above described HPLC procedure, except where noted.

The compositions of media used in the following examples are presented below.

| AS-7 Medium | g/l |
|---|---|
| thinned starch[a] | 20 |
| Ardamine pH[b] | 5 |
| Pharmamedia[c] | 15 |
| CaCO$_3$ | 2 |

| AS-7 Medium | g/l |
|---|---|

[a]Prepared by hydrolysis of starch by alpha-amylase from *Bacillus licheniformis* (available from Novo Enzymes, Wilton, CT and sold under the trademark "Termamyl") to a dextrose equivalent of 40% ± 5%.
[b]From Yeast Products, Inc., Clifton, NJ 07012
[c]From Traders Protein., Memphis, TN 38108

Adjust pH to 7.2 with NaOH.

| AP-5 Medium | g/l |
|---|---|
| thinned starch | 80 |
| Ardamine pH | 5 |
| K$_2$HPO$_4$ | 1 |
| MgSO$_4$.7H$_2$O | 1 |
| NaCl | 1 |
| CaCO$_3$ | 7 |
| FeSO$_4$.7H$_2$O | 0.01 |
| MnCl$_2$.7H$_2$O | 0.001 |
| ZnSO$_4$.7H$_2$O | 0.001 |
| P-2000 (antifoam)[a] | 1 ml/l |

[a]From The Dow Chemical Co., Midland, Michigan 48640

Adjust pH to 6.9 with 25% NaOH.

EXAMPLES 1–4

Avermectins from *Streptomyces avermitilis* I-3 (ATCC 53567)

*S. avermitilis* I-3 (ATCC 53567) from a sporulated V-8 plate as inoculated into 80 ml of AS-7 medium in a 500 ml triple-baffled flask. The flask was incubated on a rotary shaker with agitation at 200 rpm at 28°–30° C. After 24 hours of incubation, 1 ml of whole broth was inoculated into 300 ml flasks containing 40 ml AP-5 medium. Duplicate fermentations were performed at 28°–30° C. in the presence of 400 ppm of each of the primer compounds listed below, added after 24 hours.

After 312 hours, 2 ml samples of whole broth were mixed with 8 ml of methanol:acetonitrile (390:35). After filtration, 50 ul samples were injected onto a Beckman Ultrasphere ODS column (3.9×250 mm). The column was eluted with methanol:acetonitrile:water (89:14:7) at 0.8 ml/min and the eluate monitored with uv detection at 240 nm. The retention times of the novel avermectins are shown below.

| Primer Compound | Avermectin Retention Time (Minutes) | | | |
|---|---|---|---|---|
| | B2 | A2 | B1 | A1 |
| 1) ±2-methyl butyric acid | *11.60, 12.40 | *14.75, 16.10 | 23.1 | 29.82 |
| 2) cyclopentane-carboxylic acid | 12.32 | 15.86 | 25.28 | 32.96 |
| 3) cyclohexane-carboxylic acid | 14.84 | 19.26 | 31.46 | 41.14 |
| 4) +2 methyl-butyric acid | 11.60 | 14.75 | 23.1 | 29.82 |

*Both +methylbutyric acid and −methylbutyric acid are incorporated into avermectins. Under the chromatography conditions adopted, resolution of the + and − avermectins is achieved only with B2 and A2.

EXAMPLE 5

Cyclohexyl Avermectins from Streptomyces avermitilis 7881 (ATCC 53692)

A frozen vial of culture *S. avermitilis* 7881 (ATCC 53692) was inoculated into 100 ml of AS-7 medium in a 500 ml triple-baffled flask. The flask was incubated on a rotary shaker with agitation at 200 rpm at 28°–30° C. After 28 hours of incubation, 5 ml of the whole broth was inoculated into another 100 ml of AS-7 medium or a 500 ml triple-baffled flask. The flask was again incubated on a rotary shaker with agitation at 200 rpm at 28°–30° C. After 24 hours of incubation, 1 ml of whole broth was inoculated into a 300 ml flask containing 40 ml of AP-5 medium. The flasks were incubated at 28°–30° C. at 200 rpm. After 24 hours, 400 ppm of cyclohexane carboxylic acid were added, after 312 hours 2 ml samples were taken and subjected to high performance liquid chromatography as described in Example 1. Under these conditions, the only avermectin components detected in the fermentation were eluted at 14.84 (54.9 mg/l) and 31.46 (32.1 mg/l) minutes corresponding to cyclohexyl B2 and B1, respectively.

EXAMPLE 6

Sec-Butyl Avermectins from *Streptomyces avermitilis* 7881 (ATCC 53692)

The procedure of Example 5 was repeated but using 400 ppm of ±2-methylbutyric acid in place of cyclohexanecarboxylic acid, all other conditions were the same as those described in Example 2. Only sec-butyl avermectin B2 (11.60, 12.40 minutes, 63.5, 42.4 mg/l), and sec-butyl avermectin, B1 (23.1 minutes, 105.5 mg/l) were detected in the fermentation.

EXAMPLE 7

Repetition of the procedure of Example 5 but using the primer compounds listed below affords the B2 and B1 avermectins wherein the 25-substituent corresponds to the R group of the primer acid RCOOH or precursor thereto.

| Primer Compound | R |
|---|---|
| 2-methylpent-4-enoic acid | 4-penten-2-yl |
| 1-cyclohexene carboxylic acid | cyclohexen-1-yl |
| thiophene-2-carboxylic acid | thien-2-yl |
| 3-furoic acid | 3-furyl |
| cyclobutane carboxylic acid | cyclobutyl |
| cyclopentane carboxylic acid | cyclopentyl |
| cycloheptane carboxylic acid | cycloheptyl |
| 3-cyclohexene-1-carboxylic acid | cyclohex-3-enyl |
| 2-methylthiopropionic acid | 1-methylthioethyl |
| thiophene-3-carboxyic acid | thien-3-yl |
| hydroxymethylcyclopentane | cyclopentyl |
| 3-thiophene carboxaldehyde | thien-3-yl |
| 3-cyclohexylpropionic acid | cyclohexyl |
| 3-cyclopentylpropionic acid | cyclopentyl |
| hydroxymethylcyclobutane | cyclobutyl |
| 3-cyclopentyl-1-propanol | cyclopentyl |
| cyclobutylmethylamine | cyclobutyl |
| ethyl cyclobutane-carboxylate | cyclobutyl |
| 2-(cyclobutylcarbonyl)-propionic acid | cyclobutyl |
| ethyl 2-(3-thiophene carbonyl)propionate | thien-3-yl |
| 1-methylcyclopropane carboxylic acid | 1-methylcyclopropyl |
| 2-methylpent-2-enoic acid | 2-penten-2-yl |
| 2-furoic acid | 2-furyl |
| 5-methylthiophene-2-1-methylcyclopropane carboxylic acid | 5-methylthien-2-yl 1-methylcyclopropyl |
| cyclopropane carboxylic acid | cyclopropyl |
| 2,3-dimethylbutyric | 1,2-dimethylpropyl |
| 2-methylhexanoic acid | hex-2-yl |
| 2-cyclopropyl propionic acid | 1-cyclopropylethyl |
| 4,4-difluorocyclohexane carboxylic acid | 4,4-difluoro-cyclohexyl |
| 4-methylenecyclohexane carboxylic acid | 4-methylene-cyclohexyl |
| 3-methylcyclohexane carboxylic acid (cis/trans) | 2-methylcyclohexyl |
| 1-cyclopentene carboxylic acid | cyclopenten-1-yl |
| tetrahydropyran-4-carboxylic acid | tetrahydropyran-4-yl |
| 2-chlorothiophene-4-carboxylic acid | 2-chlorothien-4-yl |
| (S)-2-methylpentanoic acid | (S)-pent-2-yl |
| (R)-2-methylpentanoic acid | (R)-pent-2-yl |
| 2-furaldehyde | 2-furyl |
| cyclobutylmethylamine | cyclobutyl |
| cyclopentane carboxamide | cyclopentyl |
| ethylcyclopentane carboxylate | cyclopentyl |

We claim:

1. A mutant strain of *S. avermitilis* which produces only B avermectins when cultured under aerobic conditions in an aqueous nutrient medium comprising in addition to an assimilable source of carbon, nitrogen and inorganic salts, an acid of the formula RCOOH, or a precursor of said acid having the formula R—$(CH_2)_n$—Z wherein n is 0, 2, 4 or 6; Z is —$CH_2OH$, —CHO, —$COOR^4$, —$CH_2NH_2$ or —$CONHR^5$ wherein $R^4$ is ($C_1$–$C_6$) alkyl; $R^5$ is hydrogen, ($C_1$–$C_4$) alkyl, —CH(COOH)$CH_2$COOH, —CH(COOH)$(CH_2)_2$COOH or —CH(COOH)$(C_2)_2SCH_3$ and wherein R is isopropyl or S-sec butyl;

wherein said strain is obtained by a process which comprises mutating *Streptomyces avermitilis* ATCC 53567; and selecting a mutant which lacks branched-chain 2-oxo acid dehydrogenase activity and avermectin B O-methyltransferase activity.

2. A biologically pure culture of *Streptomyces avermitilis* which lacks branched-chain 2-oxo acid dehydrogenase activity such that permeabilized cells thereof are unable to produce $^{14}CO_2$ from [$^{14}C$-1]-2-oxoisocaproic acid added thereto and which lacks avermectin B O-methyltransferase activity such that said *S. avermitilis* produces essentially only B avermectins.

* * * * *

UNITED STATES PATENT AND TRADEMARK OFFICE
CERTIFICATE OF CORRECTION

PATENT NO.  : 5,565,359
DATED       : October 15, 1996
INVENTOR(S) : Edmund W. Hafner et al.

It is certified that error appears in the above-identified patent and that said Letters Patent is hereby corrected as shown below:

Column 3, line 65 - "[$^{14}$C-1]-2-oxo-3-methylvaletic" should read -- [$^{14}$C-1]-2-oxo-3-methylvaleric --.

Column 18, line 50 - "-CH(COOH)(C$_2$)$_2$SCH$_3$," should read -- -CH(COOH)(CH$_2$)$_2$SCH$_3$, --.

Signed and Sealed this

Eleventh Day of March, 1997

Attest:

BRUCE LEHMAN

*Attesting Officer*      Commissioner of Patents and Trademarks